United States Patent [19]

Naftulin

[11] 4,060,107

[45] Nov. 29, 1977

[54] METHOD AND APPARATUS FOR COLLECTING FLUIDS

[76] Inventor: Henry Naftulin, 8341 N. Kenton Ave., Skokie, Ill. 60076

[21] Appl. No.: 735,764

[22] Filed: Oct. 26, 1976

[51] Int. Cl.² .................. B65B 31/02; A61M 1/00
[52] U.S. Cl. .................. 141/7; 128/276; 141/10; 141/51; 141/59; 141/114
[58] Field of Search .................. 128/276, 278, 214 R, 128/214 D; 73/421 R; 137/205; 141/5, 7, 8, 10, 51, 59, 114, 313-317; 220/63 R, 85 A, 85 B, 17; 206/522

[56] References Cited

U.S. PATENT DOCUMENTS 3,814,098  6/1974  Deaton .................. 128/276

Primary Examiner—Richard E. Aegerter
Assistant Examiner—Frederick R. Schmidt
Attorney, Agent, or Firm—Joel E. Siegel

[57] ABSTRACT

A method and apparatus for collecting fluids into flexible containers. The apparatus includes an outer vacuum chamber having a flexible container disposed therein. A split inner chamber is positioned around the flexible container. A bladder means is disposed between the inner chamber and the outer chamber. The bladder means is in communication with the atmosphere so as to cause the bladder means to expand and fill the space between the inner chamber and the outer chamber when the vacuum is applied to the outer chamber.

7 Claims, 4 Drawing Figures

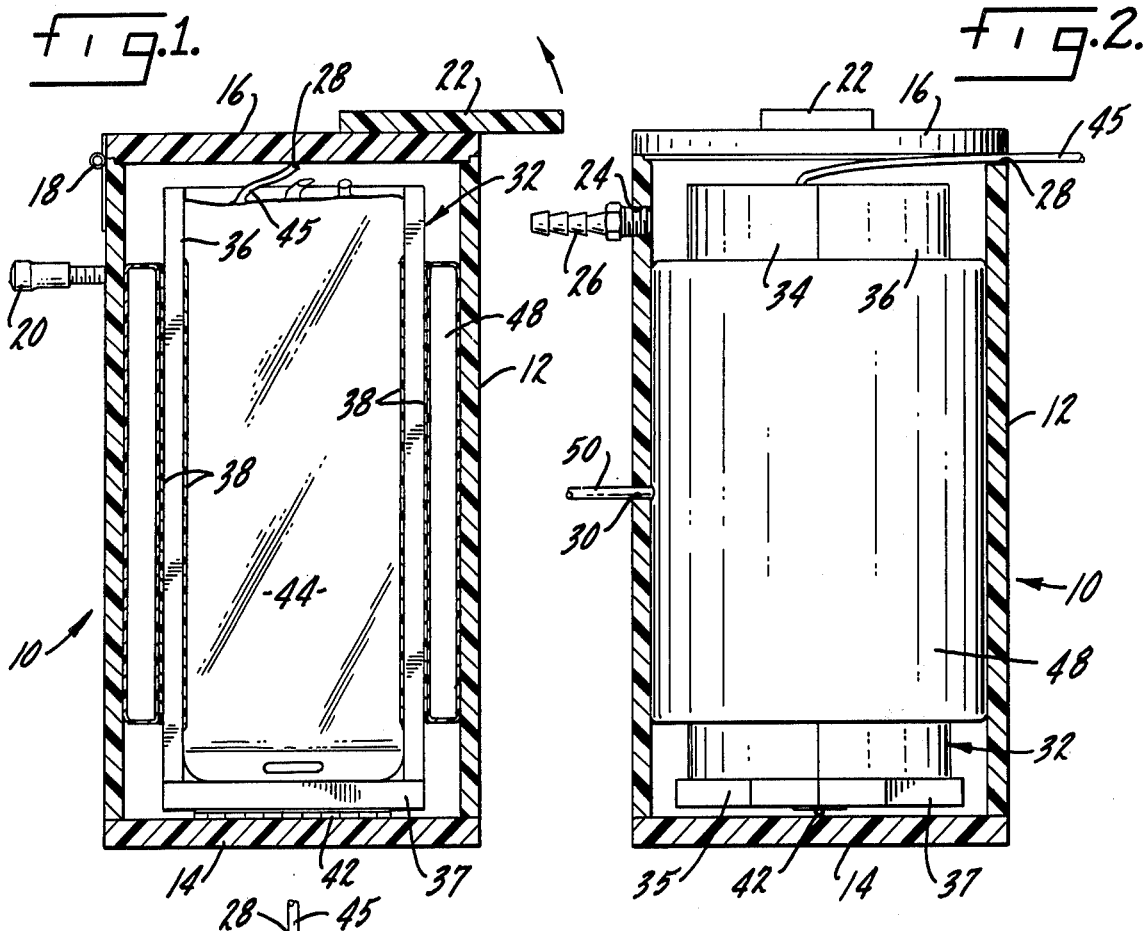
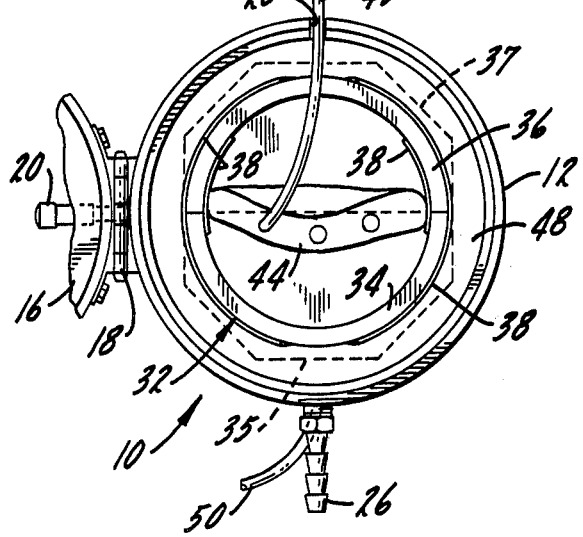
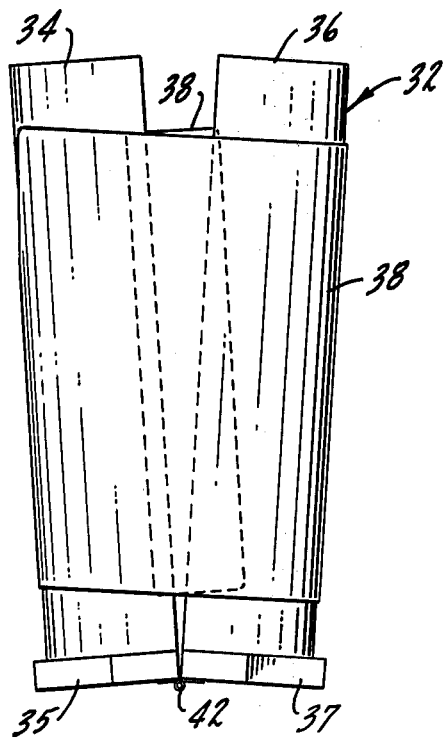

METHOD AND APPARATUS FOR COLLECTING FLUIDS

BACKGROUND OF THE INVENTION

This invention relates to the collection and storage of biological fluids. The invention more particularly relates to a unique method and apparatus for collecting fluids such as blood, serum, plasma and the like into flexible containers made from plastic, rubberized cloth and the like.

In accordance with conventional practices, blood is taken from human donors or animals and stored in sterilized glass bottles and/or flexible containers. Blood is removed from the body of the donor through a phlebotomy needle inserted into a vein, the needle being connected to the storage container by means of flexible tubing. The glass bottles which are used for this purpose require special construction and are therefore relatively costly. In order to reuse these bottles a careful sterilization process must be effected using special equipment. Further glass bottles are easily breakable and are not adapted to fit into small or irregular spaces.

In recent years, the use of flexible containers have found wide spread use for the storage of blood. The most commonly used type of flexible containers are manufactured from a plastic material. Collapsible containers by their very nature are incapable of being previously evacuated. To solve this problem, the flexible containers have been used in conjunction with blood extracting equipment which includes a vacuum chamber designed to receive the flexible container therein. The vacuum chamber includes means for drawing vacuum therein during the extracting operation. This type of system permits the collection of blood into a flexible container under the influence of a vacuum. However, as the flexible container is being filled, it expands in volume into contact with the sides of the vacuum chamber making it quite difficult to remove the blood filled container from the chamber upon completion of the blood draw. If the vacuum chamber is increased in size to solve the above problem then there is no control of the upper limit of the quantity of blood drawn.

In order to disclose the present invention in an environment which utilizes its potential to a maximum, it will be disclosed for use in the collection of blood from an animal, such as a fetal calf. It has been the heretofore practice to collect blood from the fetal calf in glass vacuum bottles of the type mentioned hereinabove. In addition to the disadvantages previously mentioned with regard to glass bottles, they are of fixed dimensions and can only collect a fixed amount of blood. Since the size of the fetal calf and the amount of blood available to be collected varies considerably, it has heretofore been sometimes necessary to puncture the calf a second time to maximize the blood drawn from each calf. A second puncture increases evacuation time and the chances of contamination. A further problem which has presented itself is that the use of conventional glass bottles frequently results in hemolysis. The initial excess vacuum present in the bottle causes rupture of certain blood cells which releases hemoglobin into the collected blood, which substantially reduces its use in many medical applications.

Although the present invention will be hereinafter described in the environment of collecting blood from a fetal calf for purposes of disclosing a specific use, it is contemplated that the teachings of the invention are equally applicable for drawing various types of biological fluids from humans and other animals.

SUMMARY OF THE INVENTION

It is a primary object of the present invention to provide an improved method and apparatus for collecting and storing biological fluids in flexible containers.

It is a further object of the invention to provide a biological fluid collection and storage apparatus which can accomodate the collection of varying quantities of fluid.

Another object of the invention is to provide a biological fluid collection apparatus which reduces the likelihood of hemolysis.

A still further object of the invention is to provide an improved method and apparatus for withdrawing biological fluid from a donor into a flexible container positioned within a vacuum chamber which permits the easy withdrawal of the full flexible container from the vacuum chamber.

It is also an object of the invention to provide a biological fluid collection apparatus which permits the control of the amount of fluid withdrawn from the donor.

The apparatus in accordance with the present invention includes a rigid outer chamber having a flexible container disposed therein for receipt of the collected fluid therein upon the creation of a vacuum within the outer chamber. A split inner chamber is provided around the flexible container within the outer chamber. Bladder means are disposed between the inner chamber and the outer chamber. The bladder means is in communication with the atmosphere so as to cause the bladder means to expand and fill the space between the inner chamber and the outer chamber when the vacuum is applied to the outer chamber.

BRIEF DESCRIPTION OF THE DRAWINGS

These and other objects and advantages of the invention will become apparent from the following description when taken in connection with the accompanying drawings. In the drawings, wherein like reference numbers have been used to indicate like parts throughout:

FIG. 1 is a vertical sectional view taken through a central portion of the apparatus constructed in accordance with a preferred embodiment of the present invention;

FIG. 2 is a side elevational view, partially broken away, of the apparatus shown in FIG. 1 rotated ninety degrees about the vertical axis;

FIG. 3 is a top plan view of the apparatus as shown in FIG. 1 with the top in its open position; and FIG. 4 is an elevational view of the split inner chamber shown in FIG. 2 in its split or open position.

DESCRIPTION OF A PREFERRED EMBODIMENT

Referring now to the drawings and in particular to FIGS. 1-3, there is shown an apparatus for collecting and storing biological fluids in accordance with and embodying the principles of the present invention, the apparatus generally being designated by the numeral 10. Apparatus 10 includes an outer chamber 12 of rigid construction. Any suitable material possessing the necessary strength and rigidity can be utilized in fabricating chamber 12. Examples of suitable materials on construction are glass, plastics, metals and the like. A transparent plastic material is a preferred material of construction for the outer chamber 12.

In the form of the invention shown in the drawing, chamber 12 is cylindrically shaped and closed at one end by bottom portion 14 and open at the other end. A top lid 16 is pivotally secured to the outer wall of chamber 12 adjacent its upper end through hinge member 18. Lid 16 is designed to pivot between a closed position, as shown in FIG. 1, and an open position, as shown in FIG. 3. A stop member 20 is preferably secured to chamber 12 to support lid 16 in its open position. A handle 22 is secured to lid 16 to facilitate movement between its open and closed positions.

An opening 24 is provided through an upper portion of chamber 12 for receipt of a tapered fitting 26 therein. Fitting 26 extends outwardly from chamber 12 and is adapted to be connected to a vacuum line (not shown) to draw a vacuum within chamber 12. An opening 28 is formed at the upper periphery of chamber 12 to permit the fluid collection line 45 to pass therethrough in manner which will herein below become more apparent. An opening 30 is also provided through an intermediate portion of chamber 12 for receipt of a bladder line 50 therethrough for reasons which will herein below become more apparent. Openings 28 and 30 are sized in relationship to lines 45 and 50 so that a vacuum can be maintained in chamber 12 without leakage around lines 45 and 50.

Positioned within chamber 12 is an inner chamber 32 which rests on the bottom portion 14. Referring to FIG. 4, inner chamber 32 in its perfered form is constructed of two opposing half cylindrical members 34 and 36 having bottom portions 35 and 37 pivotally secured together by hinge member 42. When pivoted into contact with each other members 34 and 36 define a cylindrical open top chamber 32, as shown in FIGS. 1-3. As members 34 and 36 are pivoted away from each other, as seen in FIG. 4, the volume defined by chamber 32 is increased. This feature of chamber 32 forms an important part of the invention for reasons which will herein below become more apparent. Members 34, 35, 36 and 37 may be constructed of any rigid material, but are preferrably constructed of a transparent plastic material. As best seen in FIGS. 1 and 3, protective shield members 38 are provided along the vertical edges of members 34 and 36. Shield members 38 are secured to the inner and outer surfaces of members 34 and 36 in such a manner so that as the corresponding vertical edges approach each other one shield member passes immediately inside the chamber 32 and the other shield member passes immediately outside the chamber 32. The purpose of the shield members 38 is to prevent damage to the flexible container 44 and the bladder 48 as the vertical edges of the members 34 and 36 approach each other.

Positioned within inner chamber 32 is a fluid collecting flexible container or bag 44. Container 44 is of conventional construction and may be made from many flexible materials well known in the art, the most commonly used type being manufactured from a plastic material such as polyvinyl chloride resin base material. Container 44 includes a fluid collection line 45 having one end in communication with the interior of container 44 and the other end extending through opening 28 for receipt of the collected fluid thereinto.

A flexible bladder member 48 is positioned within outer chamber 12 around inner chamber 32, as seen in FIGS. 1 and 2. Bladder 48 includes a bladder line 50 having one end in communication with the interior of bladder 48 and the other end passing through opening 30 in chamber 12 for communication with the atmosphere. THe interior of bladder 48 is thus in communication with the atmosphere through line 50. The present invention alternatively contemplates the use of a plurality of bladder members positioned around inner chamber 32 and in communication with the atmosphere.

The operation of the above described preferred embodiment of the invention will now be described as used in the collection of blood from a fetal calf. An empty flexible container 44 is positioned within inner chamber 32 which is in an open position as shown in FIG. 4. The fluid collection line 45 is extended through opening 28 and the lid 16 is lowered to its closed position, as shown in FIGS. 1 and 2. The fluid collection line 45 is then clamped off outside outer chamber 12. A vacuum is drawn in outer chamber 12 through a vacuum line (not shown) which is connected to fitting 26 at one end and a source of vacuum such as a vacuum pump (not shown) at its other end. As the vacuum is being drawn in chamber 12 the bladder 48 is caused to expand due to the fact that it is vented to atmosphere through line 50. The resultant expansion of bladder 48 exerts pressure on halves 34 and 36 of inner chamber 32 moving both halves into contact with each other to attain its closed position. Apparatus 10 is now in the condition shown in FIGS. 1-3 and ready for use to collect fluid into container 44.

To collect blood from the fetal calf a phlebotomy is performed in the fetal calf with the terminal end of collection line 45. Upon removal of the clamp from line 45, the negative pressure, created by the vacuum in outer chamber 12, against the walls of container 44 will cause it to expand and blood to be drawn into the container. THe withdrawal of blood may be carefully controlled by the regulation of the degree of vacuum drawn in outer chamber 12. An increase in the vacuum in chamber 12 will increase the flow rate of blood into container 44.

Apparatus 10 utilizes the flexibility and expandibility of container 44 as the blood is being collected. Container 44 fills and expands initially to the confines of inner chamber 32 and then continues to expand and fill vertically upward until the physical limits of the container 44 and the inner chamber 32 are reached. It can thus be seen that the amount of blood collected depends on the size of the inner chamber 32 and container 44, and the degree of vacuum within outer chamber 12. By changing or adjusting these variables the amount of blood drawn can be controlled.

After the desired amount of blood has been collected the collection line 45 is again clamped off, the vacuum pump is shut down, and the outer chamber 12 is vented to atmosphere by opening lid 16. The venting of outer chamber 12 to atmosphere causes the bladder 48 to deflate, which in turn causes the inner chamber 32 to split apart into its open position. The container 44 full with blood, which would otherwise be difficult to remove, is easily removed from the inner chamber 32 because it is no longer exerting pressure against the walls of chamber 32.

The above described operation of apparatus 10 provides numerous advances in the art of collecting blood from a fetal calf. Since the size of a fetal calf varies considerably, the amount of blood which can be collected from each donor likewise varies. Apparatus 10 permits the expansion of container 44 until the amount of blood desired is collected. The maximum limits of the amount of blood which can be drawn is limited by the dimensions of chamber 32 and container 44. Heretofore used glass containers do not permit the collection of blood beyond the physical dimensions of the glass bottle. Further, heretofore used blood collection systems, which have included a flexible container positioned within a vacuum chamber, have either not been able to control the upper limits of the amount of blood drawn or have presented extreme difficulties in removing the container from the vacuum chamber. It is important for later processing, such as centrification, that the maximum limits of the amount of blood drawn be controlled.

Another feature of the present invention is the fact that there is no initial pressure within container 44 at the start of the blood collection operation. This substantially reduces the release of hemoglobin into the collected blood. Heretofore used vacuum glass bottles have an initial vacuum within the bottle which increases the likelihood of hemolysis. Further, if the vacuum glass bottle is not filled completely with blood a residual vacuum will remain in the bottle which increases the liklehood of contamination. There can be no residual vacuum in container 44 even if the container is not full with blood.

It should also be pointed out that by controlling the vacuum within chamber 12 a gentle and steady withdrawal of blood may be obtained. By such control the likelihood of collapsing the vein wall is reduced. Needless to say the blood drawn by a vacuum glass bottle can not be controlled in this manner. Recent comparative tests have indicated that in drawing blood from fetal calves of approximately the same size using the present invention, as hereinabove described, that approximately twice the quantity of blood can be collected as that collected by using conventional glass vacuum bottles.

Although the above discussion of the present invention is described in the environment of blood withdrawal from a fetal calf, it should be appreciated that the present invention is intended for use in other environments. Apparatus 10 has equal applicability for use in collecting all types of biological fluids, such as blood, serum, plasma, etc., into flexible containers. Further, apparatus 10 is contemplated for use in transferring biological fluids from a first container to a second flexible container within a closed system to insure sterile integrity. Apparatus 10 may additionally be used to aseptically collect biological fluids into a flexible container in a manner which permits further processing of the collected fluids within the same apparatus. An example of such a situation is disclosed in copending U.S. Pat. Application Ser. No. 735,173, entitled Method and Apparatus for Defibrination of Blood, under the same inventive entity and filed on the same day as the present application.

This invention is not to be limited by the embodiment shown in the drawings and described in the description, which are given by way of example and not of limitation, but only in accordance with the scope of the appended claims.

What is claimed is:

1. Apparatus for collecting and storing biological fluids, comprising:

a. a rigid outer chamber having a fluid inlet opening and a vacuum port;
   b. a flexible container disposed within said outer chamber in communication with said fluid inlet for receipt of fluid therein upon the creation of a vacuum within said outer chamber through said vacuum port;
   c. inner chamber means disposed within said outer chamber for receipt of said flexible container therein, said inner chamber means being split into at least two sections which are movable between a closed position and an open position, said inner chamber means defining a smaller volume when in its closed position than when in its open position; and
   d. bladder means disposed within said outer chamber between said inner chamber means and said outer chamber, the interior of said bladder means being in communication through an opening in said outer chamber with the atmosphere so as to cause said bladder means to expand and fill the space between said inner chamber and said outer chamber upon the application of a vacuum to said outer chamber so as to exert a pressure on said inner chamber sections and thereby move said sections toward one another into its closed position.

2. The invention as defined in claim 1 wherein said inner chamber means comprises an open top chamber split vertically in half and pivotally connected together at its bottom.

3. The invention as defined in claim 2 wherein protective shield members are provided along the two vertical edges of each half of said inner chamber means such that as the corresponding vertical edges approach each other, one shield passes inside the inner chamber means and one shield passes outside the inner chamber means.

4. The invention as defined in claim 3 wherein said outer chamber and said inner chamber are of cylindrical shape.

5. The invention as defined in claim 1 wherein a single bladder means surrounds said inner chamber means.

6. The invention as defined in claim 1 wherein said outer chamber includes a top lid pivotable between an open and closed position.

7. A method of collecting biological fluids into a flexible container positioned within an outer vacuum chamber, comprising the steps of:

a. confining the flexible container within an inner chamber, positioned within the outer chamber, and having an open and closed position, said inner chamber when in said closed position defining a volume less than its volume when in its open position;
   b. creating a vacuum within the outer chamber;
   c. moving the inner chamber to its closed position and retaining said inner chamber in its closed position;
   d. collecting the biological fluids into the flexible container;
   e. venting the outer chamber to atmosphere;
   f. moving the inner chamber from its closed position to its open position; and
   g. removing the flexible container from the inner chamber.

* * * * *